(12) United States Patent
Spikker et al.

(10) Patent No.: US 8,784,407 B2
(45) Date of Patent: Jul. 22, 2014

(54) HAIR REMOVAL SYSTEM AND METHOD

(75) Inventors: Bart Willem Jan Spikker, Eindhoven (NL); Rieko Verhagen, Eindhoven (NL); Robbert Adrianus Maria Van Hal, Eindhoven (NL); Natallia Eduardauna Uzunbajakava, Eindhoven (NL); Aleksey Kharin, Eindhoven (NL); Bastiaan Wilhelmus Maria Moeskops, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 665 days.

(21) Appl. No.: 12/922,707

(22) PCT Filed: Mar. 13, 2009

(86) PCT No.: PCT/IB2009/051045
§ 371 (c)(1),
(2), (4) Date: Sep. 15, 2010

(87) PCT Pub. No.: WO2009/115964
PCT Pub. Date: Sep. 24, 2009

(65) Prior Publication Data
US 2011/0022039 A1    Jan. 27, 2011

(30) Foreign Application Priority Data
Mar. 21, 2008    (EP) .................................. 08153173

(51) Int. Cl.
*A61B 18/18*    (2006.01)
(52) U.S. Cl.
USPC ............................................................ 606/9

(58) Field of Classification Search
CPC ............. A61Q 5/02; A61Q 5/12; A16B 18/18
USPC .............................. 606/2–19, 133; 607/88–94
See application file for complete search history.

(56) References Cited

U.S. PATENT DOCUMENTS 4,216,775 A * 8/1980 Cottingham .................... 606/36
4,880,001 A * 11/1989 Weinberg ........................ 606/11
5,606,798 A   3/1997 Kelman
6,172,795 B1 * 1/2001 Carlson ......................... 359/290

(Continued)

FOREIGN PATENT DOCUMENTS

EP    0933096 A2    8/1999
EP    1031324 A1    8/2000
FR    2826462 A1    12/2002

(Continued)

*Primary Examiner* — Gary Jackson
*Assistant Examiner* — Jeffrey Lipitz

(57) ABSTRACT

The invention relates to a system and method for removing hair. The hair removal system comprises a hair detection device and a hair removal device (20; S3) operatively coupled to the hair detection device, wherein the hair detection device comprises an imaging device comprising a first image sensor (12; S1) which is constructed and arranged to detect an image of a part of a skin (30) to be treated, and a control unit (18) adapted to discern, in the image, a hair (32) on the part of the skin (30), and operatively coupled to the hair removal device (20; S3) so as to control its operation, characterized by preventing means coupled to the control unit (18) and being adapted to disable the hair detection device or the hair removal device during a preventing period after the control unit has discerned the respective hair for the first time.

17 Claims, 5 Drawing Sheets

(56) References Cited

U.S. PATENT DOCUMENTS

| | | |
|---|---|---|
| 6,533,774 B1 * | 3/2003 | Ota ................................. 606/9 |
| 6,676,654 B1 * | 1/2004 | Balle-Petersen et al. ......... 606/9 |
| 2004/0158300 A1 * | 8/2004 | Gardiner ........................ 607/88 |
| 2004/0230186 A1 | 11/2004 | Obrebski |
| 2006/0116669 A1 * | 6/2006 | Dolleris ........................ 606/17 |
| 2007/0100401 A1 | 5/2007 | Lin |
| 2008/0051773 A1 | 2/2008 | Ivanov et al. |

FOREIGN PATENT DOCUMENTS

| | | |
|---|---|---|
| WO | 9917668 A1 | 4/1999 |
| WO | 0053261 A1 | 9/2000 |
| WO | 0062700 A1 | 10/2000 |
| WO | 2007013008 A1 | 2/2007 |

* cited by examiner

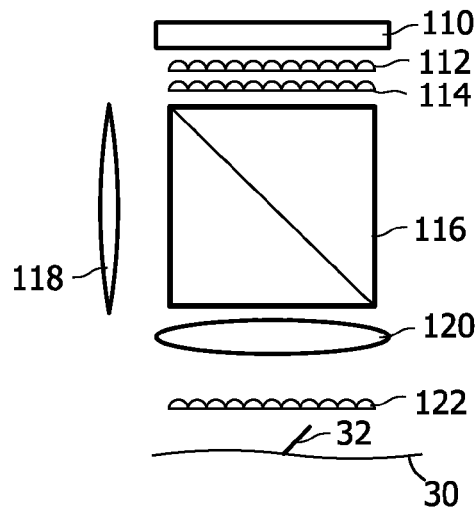
FIG. 7
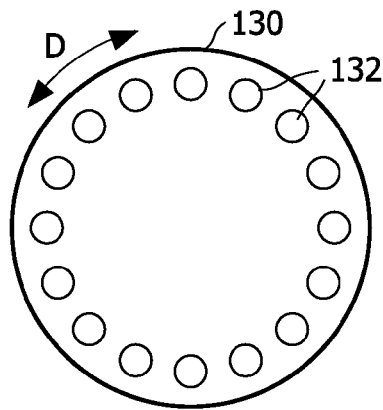
FIG. 8
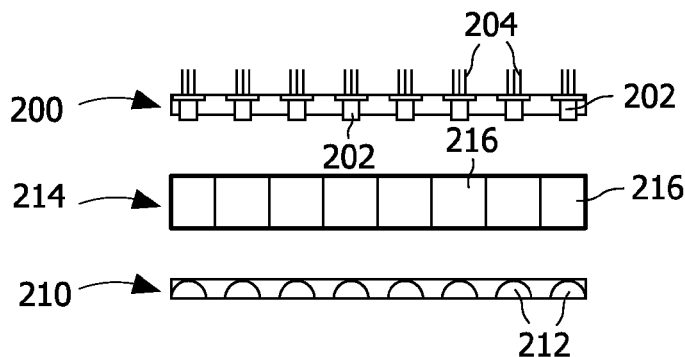 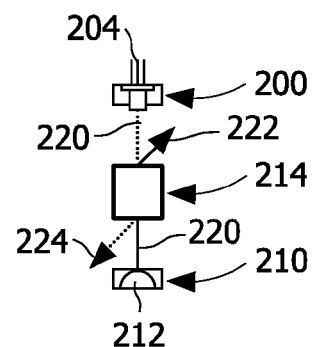
FIG. 9a  FIG. 9b

HAIR REMOVAL SYSTEM AND METHOD

FIELD OF THE INVENTION

The invention relates to a hair removal system and method. The system can, for instance, shave, cut, or permanently remove human or animal hair. The hair removal system may comprise, for instance, an assembly of a hair detection system and a laser-based shaving device.

BACKGROUND OF THE INVENTION

In a known hair removal system, hairs are detected by, for instance, an optical detection system. After detection of one hair, a light beam is focused on the hair so as to cut or remove it by destroying the hair root. An example of a method of cutting hair using a laser light source is known as Laser Induced Optical Breakdown (LIOB).

WO-00/62700 provides a system comprising a hair detection device and a hair removal device which is operatively coupled to the hair detection device. The hair detection device comprises an imaging device with a first image sensor. The imaging device is arranged to provide an image of a part of the skin to be treated. A control unit is arranged to discern, in the image, a hair on the skin part. The control unit is operatively coupled to the hair removal device so as to control its operation. The system includes a laser source and an adjustable beam manipulator. The image sensor comprises a CCD or a CMOS sensor.

WO-2007/013008-A1 in the name of the same applicant provides improved determination of the position and orientation of a hair and the speed at which this is done. The system is able to determine the position of a skin hair in three dimensions. A first image sensor is used to roughly determine the position and/or orientation of the hair. A second image sensor is used to more precisely determine the position and/or orientation of the hair in three dimensions. By using the sensor results of the first sensor, it is possible to limit the time required for the more precise but slower scanning operation by the second image sensor, provided the latter only needs to image a selected part of the part of the skin that is imaged by the first sensor. The selection may be carried out by the control unit which may be provided with image-processing software and/or hardware.

The first image sensor is constructed to provide a substantially two-dimensional image. Image sensors that are able to provide such information are relatively simple and operate quickly. In particular, the first image sensor comprises a 2D optical image sensor, preferably a charge-coupled device, a CMOS device or a focal plane array of photo detectors.

The light source may comprise, for instance, a LED or a laser light source. A LED is very compact and energy-efficient, and emits radiation within a relatively small wavelength band. This allows easy filtering, or any other control of radiation, where desired. Furthermore, LEDs are easily controllable and have a relatively long service life. A laser source may have a high power density and emits substantially monochromatic radiation, which is very well controllable by means of dedicated mirrors, filters, etc. Lasers are thus also suited for scan-imaging purposes. The obtainable power density is sufficiently high to cut or remove human or animal hair.

The systems described above are able to produce a light beam for removing hair. In one embodiment, the light beam may be directed at the root of the hair in order to destroy the root. The hair will subsequently drop off the skin. In this embodiment, the system includes an epilating device. In another embodiment, the light beam is directed to a target position on the visible part of the hair, i.e. the part of the hair that extends from the skin. The light beam will burn through the hair at the target position. In the latter embodiment, the system includes a shaving or cutting device.

Although the hair removal devices described above provide many advantages over the prior art, the light beam may be aimed at the same hair more than once. Aiming the light beam at the same hair is possible because the hair will remain in or on the skin after the light beam has been directed at the hair or at the hair root. The hair may then be detected twice or more times. Aiming the light beam at the same hair more than once is disadvantageous in view of an increased power consumption and possible skin damage or even injury.

A single hair may be detected, for instance, twice or more times due to the relation between the hair diameter and the resolution of the system. A hair having a diameter of, for instance, 100 µm may be detected at least four times if the system has a resolution of 20 µm. If the cutting process is induced at the center of the hair, the same hair may be detected again afterwards. For example, after cutting the hair, it is likely that the hair will not drop off, or from, the skin immediately. Subsequently, this hair may be detected and aimed at again.

OBJECT AND SUMMARY OF THE INVENTION

It is an object of the present invention to prevent the cutting light beam from being directed at the same hair more than once.

To this end, the present invention provides a hair removal system comprising:
  a hair detection device for detecting a hair on a part of a skin to be treated;
  a hair removal device operatively coupled to the hair detection device and including a light source for providing a light beam, and light-guiding means for guiding the light beam from the light source to a target position on the hair; and
  a control unit coupled to the hair detection device and the hair removal device so as to control their operation,
  characterized by
  preventing means coupled to the control unit and being adapted to prevent, during a period commencing after the light beam has been guided to the target position, at least a part of the hair detection device or the hair removal device from re-guiding the light beam to said target position.

The preventing means prevent a light pulse from being fired at the same hair more than a predetermined number of times. Dependent on the type of target hair, the predetermined number of times that is necessary to remove the target hair may be once, twice, or more times. As the invention prevents a light pulse from being fired more than a predetermined number of times, skin damage or injury is prevented and power consumption decreases. The system of the invention is more user-friendly and is, for instance, suitable for inexperienced or non-professional users. During the preventing period, the preventing means, for instance, disable firing a light pulse, or disable hair detection. Furthermore, the preventing means may recognize multiple detection of the same hair and subsequently start the preventing period.

In an embodiment, the preventing means comprise electronic delay means. The delay means implement the preventing period. The delay means may be included in one or more parts of the system wherein a signal delay prevents firing a light pulse at the same hair more than once.

In a further embodiment, the electronic delay means comprise a shift register. The shift register provides a relatively simple, readily available and low-cost implementation of the delay means.

In another embodiment, the electronic delay means include a filter comprising at least one capacitor, wherein the control unit is adapted to charge the capacitor to a peak level which is higher than a threshold level, after the control unit has discerned the respective hair for the first time. The filter provides a simple, robust and low-cost implementation of the delay means.

In a further embodiment, the time during which the capacitor is charged to a level above the threshold determines the preventing period. The discharge period comprises a charge period and a discharge period. The charge period may be longer or shorter than the discharge period.

In another embodiment, the control unit is adapted to charge the capacitor whenever the same hair is detected.

In yet another embodiment, the preventing means comprise memory means which are coupled to the control unit. The size of the memory and the refresh rate of the data contained in the memory may determine the preventing period. Several settings can be envisioned. The memory optionally comprises, for instance, a relatively simple shift register. A detection of a certain hair remains in the memory, depending on the number of positions in the register and the refresh rate. The number of positions and the refresh rate can be adapted in dependence on the application, cutting speed, etc.

In a further embodiment, the preventing means comprise deflection means which are coupled to the control unit when using the hair removal system, the deflection means being arranged between the skin and the hair detection device and/or between the skin and the hair removal device, and having a first state wherein light is allowed to pass in a predetermined direction, and a second state wherein light is deflected away from the predetermined direction. During the preventing period, the deflection means deflect light away from the path leading from the hair detection device to the skin and/or from the hair removal device to the skin, or vice versa.

The deflection means may comprise a liquid crystal device. The liquid crystal device comprises liquid crystals, such as are present in a liquid crystal display. A relatively small quantity of electric energy is sufficient to deflect light away from the predetermined light path, as described above. Moreover, the liquid crystal device is relatively small and flat and can thus be easily incorporated in existing hair removal systems.

In another embodiment, the deflection means comprise a Thermally Reversible Light Scattering (TRLS) material. Such materials can be reversibly switched from transparent to opaque states using temperature variation.

In an embodiment, the deflection means comprise a sol-gel. A sol-gel can be reversibly switched from an aqueous polymer solution to a gel by changes in environmental conditions. The aqueous solution is substantially transparent, whereas the gel deflects light. The changes in environmental conditions may include temperature variations, and variations of acidity (pH). The gel maintains its integrity during a predetermined period of time, which can be adapted to implement the preventing period.

BRIEF DESCRIPTION OF THE DRAWINGS

The above features of the invention will be elucidated with reference to the accompanying drawings, wherein:

FIG. 7 diagrammatically shows an example of an image sensor for a hair removal system;

FIG. 8 shows a rotatable array of lenses for an image sensor or a light source of the hair removal system;

FIG. 9a is a front view of an assembly including a sensor array, a lens array and light interruption means according to the present invention;

FIG. 9b is a side view of the assembly shown in FIG. 9a;

FIG. 10b diagrammatically shows a detection disable signal corresponding to the detection signal in FIG. 10a;

FIG. 11b diagrammatically shows a digitized hair detection signal corresponding to the hair detection signal in FIG. 11a.

DESCRIPTION OF EMBODIMENTS

Figure 1:
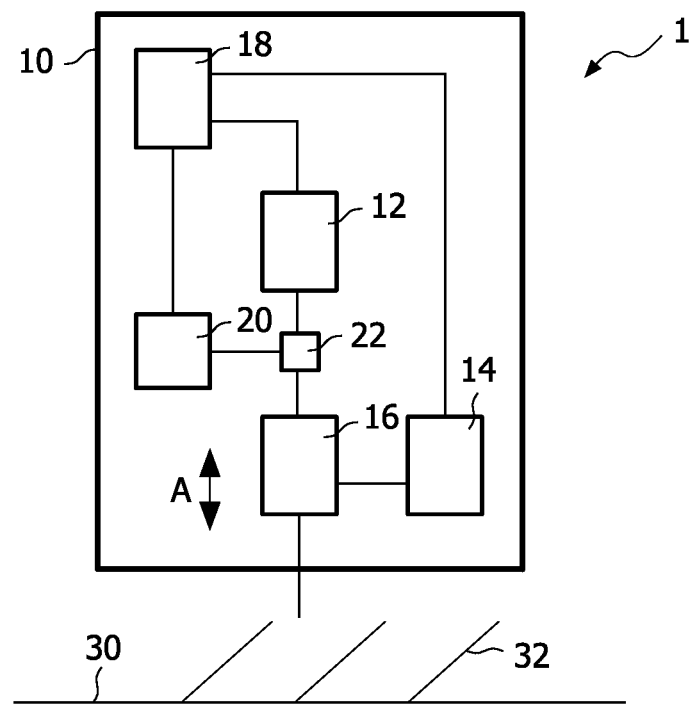
FIG. 1 diagrammatically shows an example of a hair removal system.

FIG. 1 diagrammatically shows an example of a hair removal system 1 using a light source for temporary or permanent removal of hair.

The system 1 comprises a housing 10 with a first image sensor 12, a second image sensor 14 with an adjustable lens 16, a control unit 18, a hair removal device 20 and an optical coupling 22. The separate movable lens 16 as well as the optical coupling 22 is optional, as will be explained hereinafter.

The Figure also shows a skin 30 with hairs 32 to be removed.

The housing 10 of the system 1 only comprises parts that are relevant as examples of the functioning of a hair removal system. Obviously, additional parts, such as a power unit, an optical window, etc. may be present, but are not shown.

The first image sensor 12 may comprise e.g. a CCD camera, a CMOS device, etc. The second image sensor 14 is coupled to an adjustable lens 16 and may comprise a scanning unit.

Both image sensors 12 and 14 are coupled to a control unit 18 which is constructed and arranged to discern hairs from the image as obtained by the sensors 12 and 14.

Also coupled to the control unit 18 is a hair removal device, such as a laser system, an electric epilation system, etc. The lens 16 may be moved in the direction of arrow A so as to focus at different values of z, in order to scan and produce an image in the z direction. Optionally, the adjustable lens 16 may be moved aside in a direction e.g. perpendicular to arrow A in order to free a field of view of the first image sensor 12.

Figure 2:
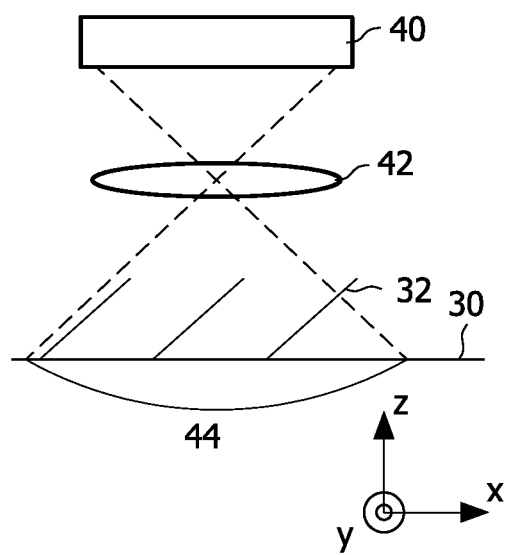
FIG. 2 diagrammatically shows a first image sensor as used in the system shown in FIG. 1.

FIG. 2 diagrammatically shows a first image sensor as used in the system. Herein, as in all Figures, similar parts are denoted by the same reference numerals. In the Figure, reference numeral 40 denotes a CCD, 42 denotes an optical system, while 44 denotes a field of view of the CCD.

In FIG. 2, more than one, i.e. three, hairs 32 are present in the field of view of the CCD, as most CCDs have fields of view of e.g. one or more cm². Such an area of e.g. a human beard contains several dozens of hairs. However, the resolution and the range in the perpendicular direction, for instance, the z direction as shown in FIG. 2 is limited and determined by the properties of the optical system 42. Note that a CCD can determine an image in one step, with all pixels being "filled" simultaneously.

As a CCD image sensor is known per se to the skilled person, its details will not be described here.

Figure 3:
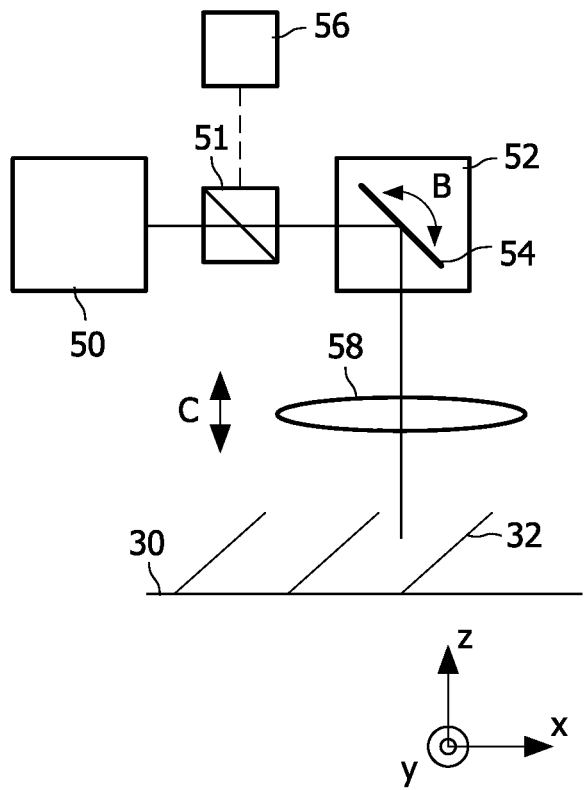
FIG. 3 diagrammatically shows a second image sensor as used in the system shown in FIG. 1.

FIG. 3 diagrammatically shows a second image sensor which may be used in the hair removal system. In this Figure, reference numeral 50 denotes a laser source, 51 denotes a beam splitter, 52 denotes a beam manipulator with a movable mirror 54 which is movable e.g. in the direction of arrow B. A detector is denoted by reference numeral 56, while a lens 58 is movable in the direction of arrow C.

Alternatively to the laser source 50, any other suitable radiation source may be selected, such as a LED with a lens. The emitted beam is partly transmitted by beam splitter 51 (which may or may not be polarizing), and partly reflected downwards e.g. to a beam dump (not shown).

Beam manipulator 52 is controllable by e.g. the control unit (not shown) and comprises a movable mirror 54, such as a polygon mirror or any other suitable type of scan mirror. As shown, the mirror 54 is movable e.g. rotatable in the direction of arrow B in order to scan a beam of radiation across a desired area, in this case a second field of view. In practice, the field of view of the second image sensor will have dimensions of about 0.5 mm×0.5 mm in the x, y directions and a similar dimension in the z direction. To obtain the latter range, the optical system or lens 58 is movable in the direction C. Alternatively, the optical system or lens 58 may be adjustable in optical power, i.e. its focal length.

The detector 56 is optically coupled to the beam manipulator 52 via the beam splitter 51. Radiation reflected, Raman-scattered, etc. at the skin 30 or hairs 32 is reflected by the mirror 54 towards beam splitter 51 and will be partly reflected towards detector 56.

The detector 56 may comprise a CCD or CMOS or any other kind of photo detector or array thereof. The detector 56 will also be coupled to the control unit (not shown) in order for the control unit to determine the position and/or orientation of a hair 32 on a skin 30. A three-dimensional image will be obtained for this second image sensor. This type of image sensor may also be referred to as a 3D scanning sensor. Further details known per se in the state of the art and being apparent to the skilled person will not be described.

Figure 4:
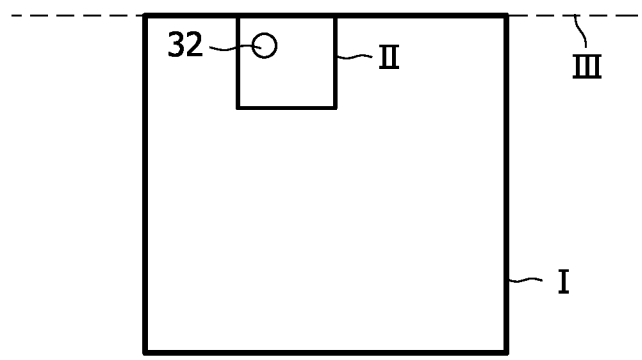
FIG. 4 diagrammatically indicates first and second fields of view, including one hair on a skin.

FIG. 4 diagrammatically indicates fields of view of the first and the second image sensor, including one hair on a skin.

The area indicated by I is a square of about 2×2 mm. It is about $\frac{1}{100}^{th}$ of the surface area of an average field of view of a CCD sensor as suggested by the broken line III. The area I of 2×2 mm represents the average surface area per hair 32 of a human beard. The hair 32 has been drawn to scale, albeit diagrammatically, with a diameter of about 120 micrometer. Also indicated is a surface area denoted by II. This denotes an average surface area as may be scanned by a present-day 3D scanner sensor. Its dimensions are about 0.5×0.5(×0.5) mm. It is clear from this Figure that a relatively small part of the total field of view of the first (CCD) sensor needs to be scanned by the second image sensor (surface area II). As the 3D scan of the latter image sensor takes relatively more time, more efficient use can be made of said second image sensor.

Figure 5:
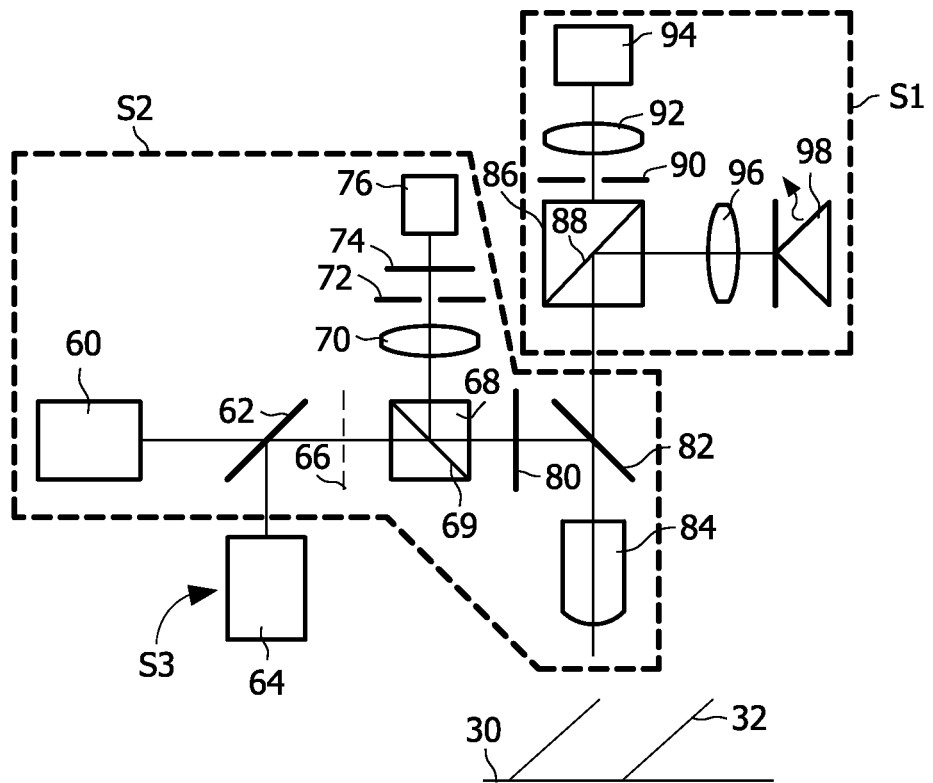
FIG. 5 diagrammatically shows an example of a detail of a hair removal system.

FIG. 5 diagrammatically shows an example of a hair removal system in more detail. In this Figure, S1 generally denotes a first image sensor, S2 denotes a second image sensor and S3 denotes a hair removal system.

The second image sensor S2 comprises a detection laser 60, a beam splitter 62, a shutter 66, a first polarizing beam splitter 68 with a first beam-splitting surface 69, a first lens 70, a first pinhole 72, a bandpass filter 74 and a detector 76. Furthermore, it comprises a λ/4 plate 80, a mirror 82, and an object lens 84.

The first image sensor S1 generally comprises a second polarizing beam splitter 86 with a second beam-splitting surface 88, a diaphragm 90, a tube lens 92 and a CCD 94, as well as a LED lens 96 and a LED 98.

The hair removal device comprises a cutting laser 64. The cutting laser 64, the detection laser 60, the detector 76 and the CCD 94 and the object lens 84 may all be connected to a control unit (not shown). Furthermore, the detection laser 60 and the cutting laser 64 may also be one and the same laser, especially if this is an adjustable laser. Moreover, various parts are optional, such as, in the latter case, beam splitter 62, shutter 66, polarizing beam splitters 68 and 86, pinholes 72 and 90, λ/4 plate 80 and mirror 82.

Light for the CCD detection method of the first image sensor S1 is emitted by the LED 98 with optional LED lens 96. Part of the radiation is reflected by the surface 88, passes the mirror 82 which is transparent to LED radiation but highly reflective to e.g. 1064 nm radiation in this case, and strikes the skin 30 with a hair 32. An image thereof is reflected and again passes the second polarizing beam splitter 86, the pinhole 90, the tube lens 92, and is detected by the CCD 94. Note that the object lens 84 is movable and may be moved out of the way. Note that light or other radiation, such as infrared radiation, may also be supplied directly, i.e. not confocally. For instance, a LED may shine directly onto the skin. In such cases, a beam splitter 86 is not required.

Figures 6A, 6B:
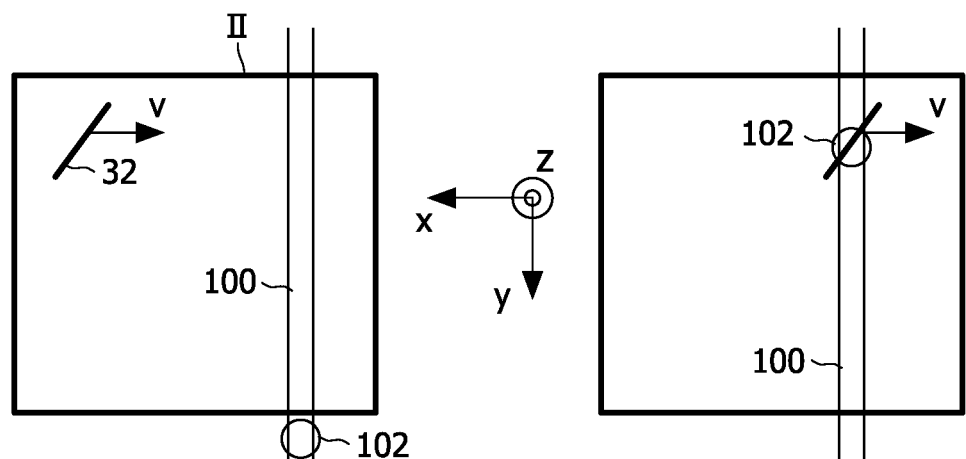
FIGS. 6a and 6b show two steps of a method of determining a hair position and cutting the hair.

FIGS. 6a and 6b show two steps of a method of determining a hair position and cutting the hair. In these Figures, II shows an image of a part of the skin, with one hair 32 present. Reference numeral 100 denotes a guiding rail and 102 denotes a movable lens.

In use, the complete system will be moved across the skin. Since movement is relative, this is shown in FIG. 6a as a hair 32 moving at a velocity v in the direction of the arrow as shown. By using the first and the second image sensor, the rough position of the hair 32 in x and y is determined. Then, the movable lens 102 is moved along the guiding rail 100 to this x,y position, see FIG. 6b, where the z position is determined by scanning. As soon as the position in three dimensions has been determined sufficiently accurately, the hair may be removed by firing a laser, electric epilation through appropriate positioning of electric needles, etc.

The following numerical example may be given with reference to the foregoing description. An average velocity v when shaving is about 5 cm/s. A useful resolution in x, y is about 20 micrometers. With a common 1000×1000 pixel camera, this would result in a total field of 2 cm×2 cm. This in turn results in a camera frame rate of 2.5 kHz, or an acquisition time of 0.4 ms. This can be easily obtained with a CMOS system. The movable lens 102 may be e.g. the lens of a DVD sled, which has a typical access time of 15 ms (66 Hz). While a DVD actuator unit has a resolution of about 20 nm, only about 20 μm of resolution is required. This less strict requirement in respect of resolution may also result in even shorter access times. The actuator for the movable lens can move the lens along the y,z direction through 1-2 mm at 5-6 kHz (0.16-0.20 ms). Once the movable lens is set to the proper position, the actuator, with the lens, can locally scan in a 3D method as explained hereinbefore. In the correct position, again, the hair may be removed by means of any suitable technique.

A limiting time of the system described above is the access time of the movable lens, which is approximately 15 ms. For a typical human beard having about 12,000 hairs, this would result in a shaving time of about 3 minutes, which is normal for a shave.

In another hair removal system, shown diagrammatically in FIGS. 7 and 8, use is made of a plurality of lenses, or lens arrays. In particular, reference numeral 110 denotes an image sensor (e.g. CCD/CMOS), while a first, second and third movable lens array are denoted by 112, 114, and 122, respectively. Reference numeral 116 denotes a polarizing beam splitter, 118 denotes a ring light aperture, and 120 denotes a lens. Various other components, such as light sources, a λ/4 plate, a control unit, etc. are not shown. Reference numeral 30 denotes skin with a hair 32.

The system shown in FIG. 7 depicts a first imaging step, the 2D imaging step. The apertures of the third lens array 122 are projected by lens 120 onto the apertures of the second lens array 114, which in turn are projected onto the apertures of the first lens array 112, which in turn are projected on the image sensor 110. Now, the image of the object, in this case skin 30, is projected on the image sensor 110 in such a way that the individual lens images are not mirrored each. Every lens produces a small part of a larger image of the object. At the same time, this lens 120 projects the light-emitting ring light aperture 118 on the third lens array 122.

Each lens array may be subjected to a substantially identical continuous motion in a harmonious fashion, e.g. rotational or vibrational, in the plane of the image sensor 110. At the same time, the whole system is moved laterally across the skin 30 by the user of the system, to perform the shaving action. In all, each lens of the three lens arrays that constitute a single facet of the imaging system generates a projection of the region of interest, or field of view, on the image sensor 110 in a repetitive manner.

Every point on the object 30, 32 within the field of view of the third lens array 122 is preferably, but not exclusively, imaged at such a frequency that the lateral displacement from scan to scan due to the user's lateral motion is roughly equivalent to, and not much more than, the intended lateral target resolution of, say, 20 μm.

The sensor 110 undergoes the same lateral displacement as the lens arrays, but not the harmonic motion. Consequently, the image of the object 30, 32, as projected on the sensor 110, moves at the same lateral speed as the lenses of the lens arrays and image sensor combination, while the harmonic (rotating, vibrating, . . . ) motion is only experienced by the lens arrays 112, 114, 122.

In the system shown in FIG. 7, the lens 120 serves to project the apertures of the third lens array 122 onto those of the second lens array 114. A considerable amount of space is thereby made available on either side of the lens 120, which space can be used for the second stage of the detection process, to be described hereinafter, and for coupling in light which is required for the image formation.

For the latter purpose, use is made in this case of the polarizing beam splitter 116. The light emitted by the ring light aperture 118 and supplied by e.g. fiber optics, a (halogen) incandescent lamp, one or more LEDs, and the like is projected by means of the additional lens 120 on the apertures of the third lens array 122 in such a way that each lens in this array illuminates its respective field of view in a more or less homogeneous fashion. In practice, this may be achieved by imaging the light from the ring light aperture 118 in the back focal plane of the lenses in the third array 122. This is preferably done by ensuring that light emanating from the aperture 118 is distributed in a similar fashion as the distribution of the plurality of lenses. This will be elucidated with reference to FIG. 8, which shows an array of lenses.

In a numerical example of showing feasibility, it is assumed that the required resolution is 20 μm, although other values may of course also be used. The speed at which the user moves the system across his skin is taken to be at most 5 cm/s. Again, these values may be adapted in other cases, causing corresponding changes to the following figures.

Let it further be assumed that the lens arrays consist of a disc of about 2 cm diameter with a plurality of 2 mm aperture lenses regularly spaced around the circumference, see FIG. 8. Although 16 lenses are shown, it is assumed in this numerical example that 25 lenses are present. In order to scan the entire ring image once, the ring of lenses must turn 360/25=14.4 degrees, indicated by arrow D. Hence, in order to achieve the desired resolution of 20 μm in the entire field, while the device is being moved at 5 cm/s, the disc must rotate at a rate of about 100 Hz, such that the area is imaged every 0.020/50 s=400 μs, or at a refresh rate of 2.5 kHz. The 2D image is recorded by means of the image sensor 110, such as a CCD or CMOS image sensor, and preferably at the same refresh rate (2.5 kHz) so that only very minor motional blurring will occur. Furthermore, at least 1000×1000 pixels are required to ensure that a surface area of 2×2 cm will be imaged with a resolution of 20 μm. Both this number and the required refresh rate are easily achievable with today's CCD and CMOS technology. It will be clear that other shapes of and values for the disc, number and aperture of lenses, etc. are possible, which will require adaptation of the other figures.

The imaging step described above is a first step in the total imaging process in which a 2D image is obtained. Note that a resolution of 20 μm or similar value is not yet required at this stage. A lower resolution may be selected, with a reduced acquisition time, as long as an approximate target position can be obtained. A more exact position, at the desired resolution, may be obtained in the second imaging step, i.e. with the second image sensor.

In the second imaging step, the presence of a specific target, such as a hair, is either detected at a specific and fixed depth (or z position), or scanned in order to determine its position and orientation in space. These options may be selected for every hair removal system of the invention. In the example described here, the first option is selected, e.g. in order to shave off hairs at a certain length. The presence of the target at the specified depth is determined e.g. by means of cross-polarized confocal laser scanning. To this end, a laser beam is aimed through a selected lens of the third lens array 122. This selected lens will focus the laser beam in a point which moves parallel to the moving lens, i.e. rotating, vibrating and the like. The lens will collimate light which is reflected back from the focal volume. When such a first, selected lens moves completely out of the laser beam, a second, neighboring lens will enter the laser beam and perform a new scan. The lateral resolution of the detection is thus dictated by the resolution of the confocal scan, and the distance between consecutive scans is determined by the speed at which the system as a whole moves across the target area of the skin. The intensity of the reflection of the orthogonally polarized light which is reflected or scattered back from the target area is confocally detected by means of the polarizing beam splitter 116 and a lens-pinhole combination, not shown here, but cf. FIG. 5. The quantity of light captured by the detector, as well as its variation as a function of the lens position and thus as a function of time, may provide information on the presence of various structures in the focal area (field of view) and thereby ascertain their 3D position and/or orientation.

Embodied as a laser shaver, the system can function as follows. The first image sensor detects an image of skin with hair, and the control unit, not shown but either an on-chip (CMOS) or a separate module, determines an approximate position of the hair or hairs on the skin. The accuracy may be about 100 or 200 µm. Once this coarse position has been established, the control unit can aim a detection laser, e.g. by means of a deflection unit (not shown but cf. 52, 54 in FIG. 3), such as a MOEMS (micro-optical-electrical mechanical system) or other type of movable mirror, and a dichroic mirror between the third rotating lens array 122 and the lens 120, towards the position on the rotating lens array where the hair was approximately found.

Next, the control unit records the results from the confocal laser scan and interprets the results, i.e. the second imaging step. Once the presence and position of the hair has been established by the cross-polarized 3D detection method, and when it has been determined that the position of the hair relative to the lens focus is within the desired accuracy, the detection system enables the cutting laser which emits continuous or pulsed laser radiation coupled into the lens collinearly or at a known angle and is thus focused at the original detection laser focal spot or at a known distance from that focus, respectively. The radiation from the cutting laser then cuts the hair.

Various aspects of the methods and devices as described above, without explicitly mentioning them here, may be employed or varied by the skilled person. For example, it will be clear that it is advantageous if the detection laser beam passes only one lens of the lens array or arrays at a time; in other words, the laser beam diameter is preferably smaller than the lens pitch so as to avoid ambiguous detection results. Furthermore, the shape of the disk 130, the number, pitch and size of the lenses 132, their motion, etc. may all be varied in the method, as long as the required corresponding quantities, etc. are also adapted. Even more explicitly, the above-described example only serves to show the applicability of the hair removal system. Furthermore, in all of the above, a preferred method of removing hairs was cutting them with a laser beam. However, other ways of removing hair are also possible in the context of the invention, such as electrical depletion, or only damaging the hairs or their roots, etc. In all cases, knowing the exact position, and sometimes also the orientation, of individual hairs is required to remove them. Finding this position in particular in three dimensions may take much time. The final 3D position may be found by taking the first two coordinates of the first imaging step and adding a third coordinate in the second imaging step, or all of the three coordinates may be determined in the second step after a first rough estimate in the first 2D step, etc.

The present invention provides a system which includes features to prevent firing a light beam at a single hair more than once. Several embodiments of the invention are described below, followed by more specific examples of the invention.

The cutting process can be disabled temporarily and/or locally. Disabling the cutting process may be effected, for instance, by including a predetermined delay between subsequent firings of the light beam. If the light source of the system includes, for instance, a laser, it will generally take a certain time to provide the laser crystal with enough energy to lift the crystal (again) to a predetermined energy level. Depending on the application, the predetermined energy level should be sufficient to provide a laser beam that is able to cut a hair or to destroy a hair root. Due to the time required to re-energize the laser crystal, i.e. the delay time, the laser will be unable to fire again. The delay time may be adjusted for the respective application by an integrated circuit including capacitors or other signal delay means.

Including a delay circuit can be implemented, for instance, in combination with a laser crystal which substantially covers the complete field of view, or with a laser diode in combination with an addressing mechanism.

In another embodiment, the system includes a memory. The memory tracks, for instance, the times that a laser pulse is fired, and/or the target skin positions of the laser beam. The target skin positions are combined, forming a map of the skin, including all detected hairs. A subsequent pulse will be disabled until a predetermined disable time has lapsed.

The disable time is determined on the basis of a number of parameters. The parameters may include one or more of: the estimated speed of the device with respect to the skin during use (the shaving speed), the desired hair detection resolution, the refresh rate of the sensor or sensors, the number of lenses, and the average diameter of the target hair.

Let it be assumed by way of example that the shaving speed v is about v=50 mm/s. To obtain a detection resolution res. of about res.=20 µm, the skin should be imaged at a frequency f of about f=v/res=2500 Hz. The time between subsequent detections is about t=1/2500=0.4 ms.

A target hair may have a diameter of about 150 µm. At a shaving speed of about 50 mm/s, the system is able to detect the hair during about (150 µm/50 mm/s)=3 ms. Given the parameters above, the system can detect a hair a maximum number of (3 ms/0.4 ms+1)=7+1=8 times. The hair removal system preferably fires the light pulse at the middle of the hair. The system may therefore have settings to wait, for instance, about 1.5 ms after the first detection, then fire a light pulse, and to be subsequently disabled during a disable time of about 2 ms.

The above only serves as an example. Other target hair may have a substantially larger diameter of, for instance, 500 µm, or a smaller diameter. The control circuit 18 will optionally include a number of predetermined settings, wherein each setting is optimized, for instance, for a certain hair diameter and/or density of the hairs on the skin. The system can thus be used by different people and on different parts of the body.

Using the above-mentioned map, including all the skin positions stored in the memory, the hair-cutting process can be disabled for certain addressable positions. An example of an addressable LED array is provided below.

In one embodiment, the system is adapted to interrupt signals to one or more of the light sources. A driving circuit for driving the light source may, for instance, block the drive signal to the respective light sources. Otherwise, the system may include a separate blocking circuit for blocking the drive signals to the respective light sources.

In another embodiment, the system includes means for preventing light from reaching a photo detector. The light is blocked, for instance, during a predetermined time or until a hair detection signal drops below a predetermined level. Examples are provided below.

In yet another embodiment, the system includes deflection means which are arranged between the system and the skin. The deflection means are adapted to deflect light. The deflection means include, for instance, a transparent window which becomes non-transparent after a predetermined time. A drive signal may be applied to the deflection means. The drive signal includes, for instance, an RF signal having a certain wavelength, or an adjustable temperature. A liquid crystal display allows blocking light at predetermined positions, as included, for instance, in the above-mentioned skin map.

In a further embodiment, the system includes, for instance, a software program for recognizing multiple detections of the same hair. A memory tracks the hair detection signal for every addressable position so as to generate a map of positions, and skin hairs. Using the map, the program can recognize if detection signals are within a certain predetermined minimum distance from each other, thus indicating a multiple detection of the same hair. The map in the memory can also indicate if a light beam has been fired at a certain hair. The program will then prevent the system from firing the light beam again at the respective hair.

Specific examples of implementing the embodiments described above are disclosed below, with reference to FIGS. 9 to 11.

Example 1

Hair detection or cutting of a hair may be temporarily disabled by using deflection means which are arranged between the hair and the light source.

FIGS. 9a and 9b show LED array 200 comprising a plurality of LEDs 202. Every LED 202 is connected to a driving circuit (for instance, control circuit 18 in FIG. 1) via wiring 204. Every LED may thus be switched on or off separately. The Figure also shows lens array 210 comprising a plurality of lenses 212. The lens array may be comparable with, for instance, the lens array 122 shown in FIG. 7. The lenses 212 of the lens array 210 focus the light emitted by the LEDs 202 on a target position, such as a hair.

A liquid crystal array 214 is arranged between the LED array 200 and the lens array 210. The liquid crystal array 214 includes multiple liquid crystal elements 216, one for each LED 202 and/or lens 212. The liquid crystal elements 216 are connected to the control circuit 18 via wiring (not shown) and may be driven separately from each other. In a first state, the liquid crystal elements will be transparent, allowing light to pass and follow a predetermined light path 220 (FIG. 9b). In a second state, the liquid crystal elements deflect passing light away from the light path 220, for instance, in the direction of arrows 222, 224 (FIG. 9b).

The control circuit 18 can switch the liquid crystal elements from the first state to the second state, and vice versa. The liquid crystal array 214 and the liquid crystal elements 216 are examples of the above-mentioned deflection means. If one of the liquid crystal elements 216 is in the second state, passing light will be deflected and never reach either the hair/skin, or the CCD 110, depending on the location of the liquid crystal array in the system.

The blocking means 214 (FIGS. 9a, 9b) may include any other material that is able to switch from a transparent state to another, light-deflecting state. Examples of such materials include:
Thermally Reversible Light Scattering (TRLS) materials;
Sol-gels.

A TRLS material is a thermally sensitive material which changes from a substantially optically transmissive state to a substantially optically non-transmissive state at a predetermined temperature, and which reversibly becomes substantially optically transmissive upon cooling below a second predetermined temperature. TRLS materials are available as films which can be reversibly switched from opaque to transparent states. For inducing the transition, temperatures can be varied locally by focusing light at one or more predetermined positions.

The TRLS material may include dispersion of organic crystals in a thermoset, or a polymer. The TRLS material can absorb (laser) energy once a target temperature has been reached. In one embodiment, the polymer, or mixture of polymers, is included in a skin patch. The polymer or mixture of polymers is transparent or substantially transparent at ambient temperatures. Laser light, or a similar energy form suited for photodynamic hair-cutting, is directed through the skin patch to the target tissue as described above. As tissue in the target area absorbs energy from the therapeutic light, its temperature begins to rise. Likewise, the temperature of the skin patch begins to rise.

Once heated above a threshold temperature, the polymer or polymer mixture exhibits an optical change, and the polymer or polymer mixture becomes light-reflective, absorptive or scattering, thus reducing further energy deposition. As the energy absorbed by the tissue dissipates, the temperature of the target area decreases, and the skin patch again becomes transmissive or substantially transmissive, thereby permitting the cutting process to continue relatively unabated. Through the use of an appropriate skin patch, the actual temperature of the target tissue can be carefully controlled, while harmful side effects from excess exposure to the light source can be prevented, and the hair-cutting process can be completed without interruption.

Sol-gels include materials that are able to provide a sol-gel phase transition. Sol-gels include, for instance, aqueous polymer solutions which are transformed into gels by changes in environmental conditions, such as temperature or acidity (pH), thus resulting in situ hydrogel formation. When the hydrogel is formed under physiological conditions, it may maintain its integrity for a desired period of time.

It is convenient to summarize the polymeric systems that undergo sol-gel transitions, particularly due to temperature, while emphasizing the underlying transition mechanisms and potential delivery aspects. Sol-gels include, for instance, polymeric systems of natural or modified natural polymers, N-isopropylacrylamide copolymers, poly(ethylene oxide)/poly(propylene oxide) block copolymers, and poly(ethylene glycol)/poly(-lactide-co-glycolide) block copolymers.

Referring to FIG. 7, the deflection means 214 may be installed at any convenient location in the hair removal system. Examples include, but are not limited to:
i) between the skin 30 and lens array 122;
ii) between lens array 122 and lens 120;
iii) between lens 120 and beam splitter 116;
iv) between the light source (or aperture 118) and beam splitter 116; or
v) between the CCD 110 and lens 112.

On the one hand, the deflection means may prevent multiple detection of a certain hair by deflecting the light away from the path 220 after a first peak in the detection signal. On the other hand, the deflection means may prevent light from reaching the detection means, such as the CCD 110.

Example 2

The hair removal system may include a memory for storing detection information relating to one or more specific positions on the target skin. Every position is separately addressable, i.e. the light beam can be directed at any position separately, without affecting other positions. The memory may be included in, or coupled with, control circuit 18 (FIG. 1).

In one embodiment, the memory includes a shift register. A shift register is a group of flip flops set up in a linear fashion which have their inputs and outputs connected together in such a way that the data are shifted down the line when the circuit is activated.

The present invention includes, for instance, a serial-in, serial-out shift register. This is a relatively simple type of shift register. The data string is presented at 'Data In', and is shifted right one stage each time 'Data Advance' is brought high. At each advance, the bit on the far left (i.e. 'Data In') is shifted into the first flip-flop output. The bit on the far right (i.e. 'Data Out') is shifted out and lost. For example:

```
0000
1000
1100
0110
1011
0101
0010
```

There are four storage slots available in this arrangement; hence it is a 4-Bit Register. To give an idea of the shifting pattern, imagine that the register holds 0000 (so all storage slots are empty). The input data at 'Data In' presents 1,1,0,1, 0,0,0,0. The data advance in that order, with a pulse at 'Data Advance' each time. The data advance pulse is provided by a clock having a predetermined frequency. The left-hand column corresponds to the extreme left output pin of the flip flop, and so forth.

Consequently, the serial output of the entire register is 0,0,0,0,1,1,0,1,0,0,0,0 (including the four zeros that were already included in the register). If one were to continue to input data, the output would be exactly what was put in, but offset by four 'Data Advance' cycles. This arrangement is the hardware or software equivalent of a queue. Moreover, the whole register can be set to zero at any time by bringing reset pins high.

This arrangement performs a destructive readout, i.e. each data is lost once it has been shifted out of the extreme right bit.

The memory, including, for instance, the shift register, may implement the preventing means, and/or a means for detecting multiple detections of the same hair. For every position of the map, the memory includes a separate shift register. Each position corresponds to, for instance, an area of about 20 square μm. Together, the shift registers form a map having a detection history.

In one embodiment, whenever a hair is detected at a certain position, a logic 1 corresponding to the respective position is input into the shift register.

The shift register thus provides a detection history. The number of bits of the shift register and the clock frequency determine the accuracy of the history. The accuracy may also depend on the speed of moving the hair removal device with respect to the skin 30 (FIG. 5).

The history provided by the shift register can be used to recognize multiple detections of the same hair, depending on the accuracy and the resolution of the detection system (of the order of 10 to 30 μm). For instance, the settings can be such that logic ones being within, say, 4 bits from each other, are considered to represent a detection of the same hair. This means that, in the example of data input above (1,1,0,1,0,0,0,0), all ones are within four bits from each other and are considered to represent a detection of the same hair. After the last 1, the input comprises a series of four zeros. If the input subsequently comprises a 1, this 1 will be considered as a detection of another hair.

Besides the recognition of multiple detections, the history also increases the certainty of detection. After all, detection is more likely to be positive when the same hair is detected multiple times. To prevent firing at a non-existing hair and increase the accuracy, the settings of the hair removal system may therefore use the above by only firing at a hair that is detected, for instance, twice, or three times.

Example 3

The system of the present invention includes, for instance, electronic delay means (not shown). The electronic delay means are adapted to delay signal transfer at a suitable position within the hair removal system.

The shift register described above can be included in the electronic delay means. For every position of the map, the delay means include a separate shift register. Instead of inputting a 1 when a hair is detected, each respective shift register is provided with a logic 1 whenever a light pulse is initiated at the corresponding position, and a logic 0 in the absence of a light pulse. The cutting process is temporarily disabled at the respective position as long as the shift register contains a logic 1. The cutting process is enabled again when the register solely contains a number of zeros (0).

The number of bits in the shift register, together with the refresh rate of the bits in the register (clock frequency), determines the delay time of the cutting process.

Example 4

Figure 10A:
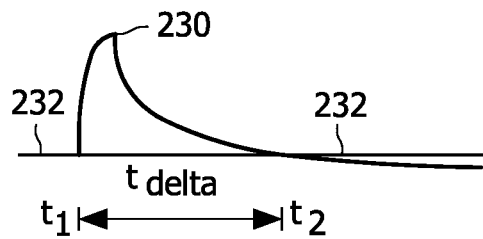
FIG. 10a diagrammatically shows a hair detection signal according to the present invention, wherein the x-axis represents time t.

In another embodiment, the electronic delay means include a filter, such as a passive RC-circuit. The filter includes at least one capacitor C and may also include one or more resistors R and/or inductors. If the system detects a hair at a certain position at time t1 for the first time (see, for instance, FIG. 3), the control circuit charges the capacitor of the RC-circuit corresponding to that position. The capacitor is charged to a predetermined detection peak level 230 (FIG. 10a). After charging, the capacitor will discharge. At time t2, the capacitor charge drops below a predetermined threshold value 232, providing predetermined discharge time $t_{delta}$. Herein, $t2-t1=t_{delta}$.

Figure 10B:
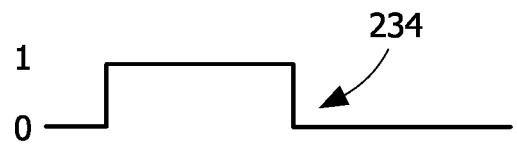

As long as the capacitor charge is higher than threshold 232, the control circuit 18 supplies a disable signal 234 at a high logic level 1 (FIG. 10b). If the capacitor charge has dropped below the threshold 232, i.e. in the example of FIG. 10a before t1 and after t2, the control circuit supplies a disable signal at a low logic level 0 (FIG. 10b). Upon detection of a hair, one light pulse will be fired. Subsequently, the control circuit disables the light beam from reaching the same hair again as long as the disable signal 234 is high level 1, i.e. during $t_{delta}$.

Disabling the light beam from reaching the hair may herein comprise any means, for instance, disabling the light source from emitting light, blocking the light beam at any stage between the light source and the hair (compare FIG. 9a), or blocking the detection signal.

Figure 11A:
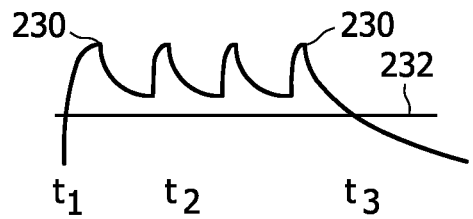
FIG. 11a diagrammatically shows a hair detection signal according to the present invention, wherein the x-axis represents time t.
Figure 11B:
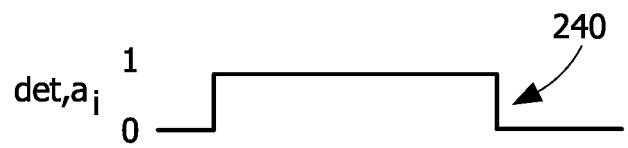

The RC-circuit may also be charged up to a peak level 230 at a first time t1 and also at every subsequent time t2 when a hair is detected (FIG. 11a). In between subsequent detections, the capacitor discharges. As long as the capacitor charge remains above the threshold 232, the control circuit 18 provides a digitized detection signal 240 at a logic high level 1 (FIG. 11b). When the capacitor charge is below the threshold 232, the digitized detection signal 240 is logic low level 0.

Figure 11C:
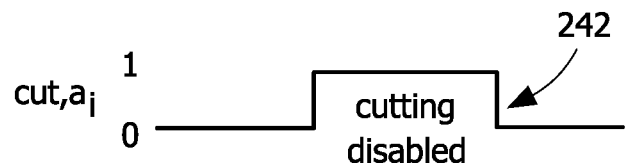
FIG. 11c diagrammatically shows a detection disable signal corresponding to the signals in FIG. 11a and FIG. 11b.

The control circuit also supplies a disable signal 242 (FIG. 11c). After detection of a hair at t1, the disable signal remains logic low level 0 during a predetermined time, for instance until t2. As long as the disable signal is low, the light beam of the light source is enabled to reach the hair. As digitized detection signal 240 remains high until t2, the control circuit raises the disable signal to a logic high level 1 as long as the digitized detection signal remains at high level 1. When the disable signal is high, the light of the light source cannot reach the hair. Cutting is thus disabled in, for instance, any of the ways described above. When the detection signal (FIG. 11a) drops below the threshold, or when the digitized detection signal returns to low level 0, the control circuit lowers the disable signal to low level 0.

Although the invention has been described above with reference to a hand-held hair removal system including an imaging device comprising an image sensor, the system may include other means for determining an irradiating position of the treatment light beam. The system of the present invention is also suitable for systems including such other determination means. Examples of such determination systems are elucidated below. Determination systems preferably use real-time and non-invasive targeting techniques.

The determination means can detect hairs based on, for instance, skin reflections. If the area of the skin part to be treated is small enough, the skin reflections will differ noticeably in the presence of a hair. The skin reflections are compared with reference skin reflections that are stored in a memory of the system so as to determine the presence of one or more hairs.

The invention has been described and elucidated with reference to examples of embodiments and the Figures. However, many modifications of the embodiments described above are conceivable within the scope of the appended claims. For instance, features of respective embodiments may be combined. The scope of the invention is determined by the appended claims.

The invention claimed is:

1. A hair removal system comprising:
   a hair detection device for detecting a first hair on a part of a skin to be treated during a detection period;
   a hair removal device operatively coupled to the hair detection device and including a light source for providing a light beam, and light-guiding means for guiding the light beam from the light source to a target position on the first hair; and
   a control unit coupled to the hair detection device and the hair removal device so as to control their operation, wherein the control unit determines the target position and activates the light source to provide the light pulse during the detection period,
   wherein a preventing means is coupled to the control unit and is adapted to prevent, at least a part of the hair detection device or the hair removal device from re-guiding a next light pulse to the first hair during the detection period.

2. The hair removal system of claim 1, wherein
   the hair detection device comprises an imaging device comprising a first image sensor which is constructed and arranged to detect an image of a part of a skin to be treated, and
   the control unit is adapted to discern a hair in the image.

3. The hair removal system of claim 1, wherein the preventing means comprise electronic delay means.

4. The hair removal system of claim 3, wherein the electronic delay means comprise a shift register.

5. The hair removal system of claim 3, wherein the electronic delay means include a filter comprising at least one capacitor, and
   the control unit is adapted to charge the capacitor to a peak level, which is higher than a threshold level, after the control unit has discerned the respective hair for the first time.

6. The hair removal system of claim 5, wherein the time during which the capacitor is charged to a level above the threshold determines the preventing period.

7. The hair removal system of claim 5, wherein the control unit is adapted to charge the capacitor whenever the same hair is detected.

8. The hair removal system of claim 5, wherein the control unit is adapted to transform the charge of the capacitor into a digitized detection signal having a logic high level when the charge of the capacitor is above the threshold level, and a logic low level when the charge of the capacitor is below the threshold level.

9. The hair removal system of claim 8, wherein the control unit is adapted to provide a disable signal for disabling hair removal when the digitized detection signal is at the logic high level during a period which is longer than a predetermined detection time.

10. The hair removal system of claim 1, wherein the preventing means comprise memory means coupled to the control unit.

11. The hair removal system of claim 10, wherein the memory means comprise a shift register.

12. The hair removal system of claim 1, wherein the deflection means comprise a liquid crystal device.

13. The hair removal system of claim 12, wherein the liquid crystal device comprises a liquid crystal array having liquid crystal elements, and
   each liquid crystal element cooperates with one respective light source of an array of light sources.

14. The hair removal system of claim 1, wherein the deflection means comprise a Thermally Reversible Light Scattering material (TRLS), or a sol-gel.

15. The hair removal system of claim 1, wherein the deflection means comprise a transparent window which becomes non-transparent after a predetermined time.

16. The hair removal system of claim 1, wherein a drive signal is applied to the deflection means.

17. The hair removal system of claim 16, wherein a drive signal comprises an RF signal having a certain wavelength or an adjustable temperature.

* * * * *